Figure 1:
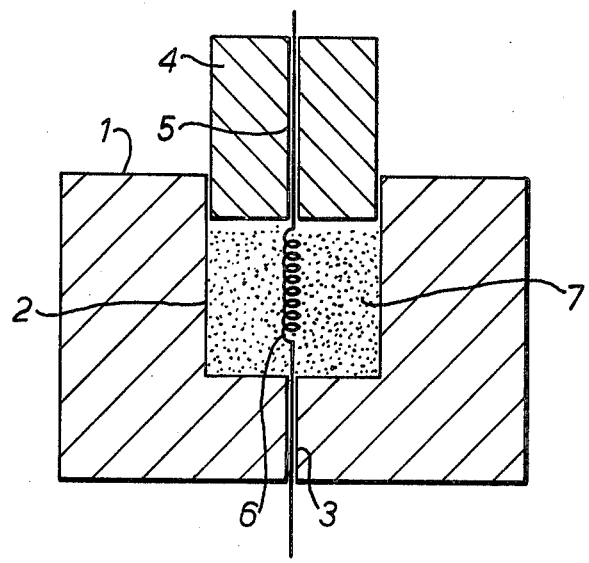

United States Patent [19]

Jones et al.

[11] 4,246,228

[45] Jan. 20, 1981

[54] COMBUSTIBLE GAS DETECTORS

[75] Inventors: Eric Jones, Chelmsford; Rodney P. Townsend, London, both of England

[73] Assignee: English Electric Valve Company Limited, Chelmsford, England

[21] Appl. No.: 936,637

[22] Filed: Aug. 24, 1978

[30] Foreign Application Priority Data

Aug. 25, 1977 [GB] United Kingdom ............... 35806/77

[51] Int. Cl.³ ..................... G01N 25/30; G01N 27/16
[52] U.S. Cl. .................................... 422/94; 23/232 E; 422/88; 422/96; 338/34
[58] Field of Search ................ 422/88, 95, 96, 97, 422/98, 119, 94; 23/232 E; 338/34

[56] References Cited

U.S. PATENT DOCUMENTS

| | | | |
|---|---|---|---|
| 3,092,799 | 6/1963 | Baker | 422/88 |
| 3,564,474 | 2/1971 | Firth et al. | 422/95 |
| 3,625,756 | 12/1971 | Taguchi | 422/88 |
| 4,111,658 | 9/1978 | Firth et al. | 422/98 |

*Primary Examiner*—R. E. Serwin
*Attorney, Agent, or Firm*—Diller, Ramik & Wight

[57] ABSTRACT

The invention relates to combustible gas detectors of the kink in which a heatable wire filament exhibits a change in resistance due to a change in its temperature caused by the oxidation of a combustible gas passing over it. In order to avoid poisoning the heatable wire filament is embedded in a pellet consisting of a homogeneous mixture of an oxidation catalyst material and zeolite material the latter preferbly of type X, Y, L or mordenite of large pore size. Additionally layers of catalytically active material and/or inactive non-catalytic porous material may be provided around the outside of the pellet.

12 Claims, 2 Drawing Figures

COMBUSTIBLE GAS DETECTORS

This invention relates to combustible-gas detectors, and concerns more particularly combustible-gas detectors of the kind in which a heatable wire filament constituting the detector element exhibits a change in resistance occasioned by the change in its temperature which occurs due to the oxidation of a combustible gas passing over it. Such detector elements are usually included in a bridge circuit, the change in the balance of which as the resistance of the wire filament changes being utilised to provide an indication of the concentration of the combustible gases.

Whilst it is possible to use as the detector element a naked wire filament it is also common to use as the element a wire filament which is embedded in a pellet of ceramic material to provide a more rugged structure. Commonly also the pellet includes an oxidation catalyst which reduces the temperature at which oxidation of the combustible gas takes place in order to reduce or prevent evaporation of the wire filament and so reduce any tendency for the characteristics of the detector to change in service. The oxidation catalyst may be provided as a layer upon a pellet of ceramic material, or, as described in the Complete Specification of our U.K. Pat. No. 1,387,412, the pellet may consist of a homogeneous mixture of an oxidation catalyst and a substantially non catalytic carrier.

A difficulty which has been experienced with detectors as described above is that in some circumstances changes in the electrical characteristics of the detector element occur in service due to poisoning of the catalyst by non-volatile residues.

The present invention seeks to provide an improved combustible gas detector which is resistant to poisoning.

According to this invention a combustible-gas detector of the kind referred to is provided wherein said heatable wire filament is embedded in a pellet consisting of a homogeneous mixture of an oxidation catalyst material and zeolite material. Said pellet may also include inactive ceramic carrier material, such as alumina, but this is not preferred.

Around the pellet consisting of a homogeneous mixture of oxidation catalyst and zeolite materials may be provided additional layers of catalytically active material and/or inactive non catalytic porous material, the latter provided to act as a molecular filter. Preferably said zeolite material comprises a zeolite of relatively large pore size (e.g. type X. Y, L or mordenite).

Preferably said zeolite material is of the hydrogen or dealuminated form.

Preferably said wire filament is of platinum and said catalytically active material is palladium and/or platinum.

Figure 2:
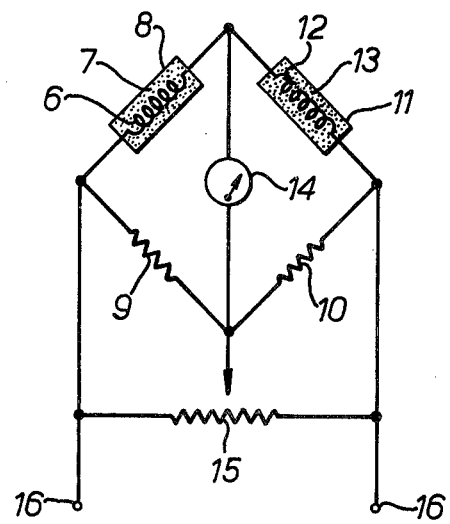

The invention is further described with reference to the accompanying drawing in which FIG. 1 is a schematic cross section of a mould being utilised to form a combustible-gas detector in accordance with the present invention and FIG. 2 is a circuit diagram of a balanced bridge arrangement (including a detector element in accordance with the present invention) for use in the detection of combustible gases.

Referring to FIG. 1, a powder is formed by a deposition of the metals palladium and platinum upon alumina powder. The product is then dried and ground to a powder. The powder is thoroughly mixed with hydrogen zeolite powder and placed in a mould 1 shown in FIG. 1. The mould shown in FIG. 1 consists of a block 1 of material having a cylindrical cavity 2 therein. In the base of the cylindrical cavity 2 a small bore hole 3 is provided, which extends to the exterior of the block 1. A plunger 4 is provided to enter the cylindrical hole 2. The plunger 4 has a small bore hole 5 passing through it, which, when the plunger 4 is within the cylindrical hole 2, is co-axial with the small bore hole 3.

To form the inventive detector element detector in accordance with the present invention, a heatable wire filament 6 is positioned within the mould with its ends extending through the small bore holes 3 and 5 in the block 1 and plunger 4 respectively. A quantity of catalytically active material is then formed by a deposition of catalytically active metals (in this case palladium and platinum upon alumina powder). The product is then ground to a powder and thoroughly mixed with zeolite powder to form a homogeneous mixture which is placed in the mould 1 as represented at 7 around the wire filament 6. Pressure is then applied to the plunger 4 which tends to compress the homogeneous mixture 7, whilst at the same time an electric current is passed through the filament 6 to provide a heating effect. The effects of pressure and heat cause the homogeneous mixture 7 to harden into a pellet to form the completed gas detector element.

Referring to FIG. 2, the gas detector element formed as above described with reference to FIG. 1 and represented at 8, is included in one arm of a balanced bridge circuit consisting of resistors 9 and 10 of equal value, and a compensating element 11. The compensating element 11 consists of a wire filament 12 embedded in a pellet 13 consisting of a homogeneous mixture of alumina and a poison, potassium hydroxide, adapted to inhibit the oxidation of combustible gases. Across the bridge is connected a voltmeter 14 calibrated to indicate combustible gas concentrations. The meter 14 is arranged to be set to zero by the adjustment of the slider on a pontentiometer 15. Terminals 16 are provided to be connected to a source of power providing both the heating current for the filaments 6 and 12 and voltage for the bridge.

Except for the nature of the detector element 8, the arrangement is, in fact, known per se. In operation, the detector element 8 and the compensating element 11 are exposed to normal atmosphere, and the slider of potentiometer 15 is adjusted to give a zero reading on meter 14. The detector element 8 and the compensating element 11 are then exposed to the atmosphere which it is required to monitor. Any combustible gases in that atmosphere oxidise on the surface of detector element 8, but not on the surface of compensating element 11, causing the temperature of the filament 6 to rise with a consequent change in its resistance. The reading of meter 14 then provides a measure of the concentration of combustible gases in the atmosphere.

A trimming resistor (not shown) may be connected in parallel with the compensating element 11, to allow for thermal differences between detector and compensating elements.

Non-volatile residues such as, for example, tetramethyl lead, deposited on the detector element 8 tend to diffuse relatively slowly through the pores of the pellet due to their relatively large molecular size, and are absorbed in the zeolite crystallites. The tetra-alkyl compounds then decompose to give non labile compounds of lead which become "fixed" in the zeolite lattice. The relatively small molecules of a combustible gas such as methane are absorbed less strongly in the zeolite crystallites, and diffuse relatively quickly through the pores of the pellet to react with the catalytically active metals.

We claim:

1. A combustible-gas detector element comprising a heatable wire filament embedded in a pellet comprising a homogeneous, cohesive heat/compression-formed mixture of oxidation catalyst particles and zeolite particles, and the oxidation catalyst particles and zeolite particles being uniformly distributed throughout the element and thereby defining like uniformly distributed pores throughout the element whereby non-volatile residues tend to diffuse relatively slowly through said pores due to their relatively large molecular size, are absorbed by the zeolite particles and upon decomposition become nonlabile compounds while relatively smaller molecules of a combustible gas are absorbed less strongly by the zeolite particles and diffuse relatively quickly through the pores of the element to react with the catalyst particles.

2. A detector as claimed in claim 1 and wherein said pellet includes inactive ceramic carrier material.

3. A detector as claimed in claim 1 and wherein around the pellet is at least one additional layer of material chosen from a group comprising catalytically active material and inactive non-catalytic porous material.

4. A detector as claimed in claim 1 and wherein said zeolite particles comprise a zeolite of relatively large pore size.

5. A detector as claimed in claim 4 and wherein said zeolite particles are of type X, Y, L or mordenite.

6. A detector as claimed in claim 1 and wherein said zeolite particles are of the hydrogen or dealuminated form.

7. A detector as claimed in claim 1 and wherein said wire filament is of platinum.

8. A detector as claimed in claim 1 and wherein said oxidation catalyst particles are chosen from a group comprising palladium and platinum.

9. A method of forming a combustible-gas detector element comprising the steps of creating a homogeneous mixture of oxidation catalyst particles and porous zeolite particles, surrounding a wire filament with the homogeneous mixture, compressing the homogeneous mixture, and heating the homogeneous mixture while the latter is under compression to form the homogeneous mixture into a relatively hard cohesive porous element.

10. The method of forming a combustible-gas detector element as defined in claim 9 wherein the heating step is performed by passing an electric current through the wire filament.

11. The method of forming a combustible-gas detector element as defined in claim 9 wherein the homogeneous mixture and wire filament are housed in a mold with ends of the wire filament projecting outwardly of the mold.

12. The method of forming a combustible-gas detector element as defined in claim 10 wherein the homogeneous mixture and wire filament are housed in a mold with ends of the wire filament projecting outwardly of the mold.

* * * * *